(12) United States Patent
Forsell

(10) Patent No.: US 10,667,918 B2
(45) Date of Patent: Jun. 2, 2020

(54) HIP JOINT DEVICE AND METHOD

(76) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 13/383,079

(22) PCT Filed: Jul. 12, 2010

(86) PCT No.: PCT/SE2010/050816
§ 371 (c)(1),
(2), (4) Date: Jan. 9, 2012

(87) PCT Pub. No.: WO2011/005197
PCT Pub. Date: Jan. 13, 2011

(65) Prior Publication Data
US 2012/0165951 A1    Jun. 28, 2012

Related U.S. Application Data

(60) Provisional application No. 61/229,738, filed on Jul. 30, 2009, provisional application No. 61/229,739, (Continued)

(30) Foreign Application Priority Data

| Jul. 10, 2009 | (SE) | 0900957 |
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900962 |
| Jul. 10, 2009 | (SE) | 0900963 |
| Jul. 10, 2009 | (SE) | 0900965 |
| Jul. 10, 2009 | (SE) | 0900966 |

(Continued)

(51) Int. Cl.
*A61F 2/36* (2006.01)
*A61F 2/34* (2006.01)
(Continued)

(52) U.S. Cl.
CPC ........ *A61F 2/3603* (2013.01); *A61B 17/1637* (2013.01); *A61F 2/32* (2013.01);
(Continued)

(58) Field of Classification Search
CPC .. A61F 2/36; A61F 2002/3625; A61F 2/3662; A61F 2002/30014
(Continued)

(56) References Cited

U.S. PATENT DOCUMENTS 3,658,056 A    4/1972 Huggler et al.
4,280,233 A *  7/1981 Raab ................ A61F 2/00
                                                     428/170

(Continued)

OTHER PUBLICATIONS

International Search Report for PCT/SE2010/050816 dated Oct. 29, 2010.

*Primary Examiner* — Bruce E Snow
*Assistant Examiner* — Melissa A Hoban

(57) ABSTRACT

A hip joint prosthesis adapted to be implanted in a hip joint of a human patient is provided. The hip joint prosthesis comprises a first area and a second area, and wherein said first area comprises a first material adapted to be elastic and said second area comprises a second material adapted to be elastic, and wherein said first material is adapted to be more elastic than said second material.

19 Claims, 8 Drawing Sheets

Related U.S. Application Data filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,735, filed on Jul. 30, 2009, provisional application No. 61/229,796, filed on Jul. 30, 2009.

(30) Foreign Application Priority Data

| Jul. 10, 2009 | (SE) | 0900968 |
|---|---|---|
| Jul. 10, 2009 | (SE) | 0900969 |
| Jul. 10, 2009 | (SE) | 0900970 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900976 |
| Jul. 10, 2009 | (SE) | 0900978 |
| Jul. 10, 2009 | (SE) | 0900981 |

(51) Int. Cl.

| A61B 17/16 | (2006.01) |
|---|---|
| A61F 2/32 | (2006.01) |
| A61F 2/30 | (2006.01) |
| A61B 17/86 | (2006.01) |
| A61F 2/46 | (2006.01) |
| A61B 17/74 | (2006.01) |

(52) U.S. Cl.

CPC ............... *A61F 2/34* (2013.01); *A61F 2/36* (2013.01); *A61F 2/3601* (2013.01); *A61F 2/3662* (2013.01); A61B 17/1664 (2013.01); A61B 17/74 (2013.01); A61B 17/86 (2013.01); *A61F 2/30734* (2013.01); A61F 2002/30014 (2013.01); A61F 2002/30069 (2013.01); A61F 2002/30471 (2013.01); A61F 2002/30507 (2013.01); A61F 2002/30558 (2013.01); A61F 2002/30563 (2013.01); A61F 2002/30565 (2013.01); A61F 2002/30579 (2013.01); A61F 2002/30729 (2013.01); A61F 2002/30733 (2013.01); A61F 2002/30878 (2013.01); A61F 2002/30886 (2013.01); A61F 2002/30922 (2013.01); A61F 2002/30968 (2013.01); A61F 2002/3241 (2013.01); A61F 2002/3483 (2013.01); A61F 2002/3615 (2013.01); A61F 2002/3631 (2013.01); A61F 2002/4631 (2013.01); A61F 2002/4635 (2013.01); A61F 2002/4677 (2013.01)

(58) Field of Classification Search

USPC .................................. 623/22.4, 22.32, 23.15
See application file for complete search history.

(56) References Cited

U.S. PATENT DOCUMENTS

| 4,283,799 | A | * | 8/1981 | Pratt, Jr. | A61F 2/30907 623/23.37 |
|---|---|---|---|---|---|
| 4,693,721 | A | * | 9/1987 | Ducheyne | A61F 2/30907 419/24 |
| 4,997,444 | A | | 3/1991 | Farling | |
| 5,030,233 | A | * | 7/1991 | Ducheyne | A61F 2/30907 623/23.54 |
| 5,181,930 | A | * | 1/1993 | Dumbleton | A61F 2/30965 623/23.34 |
| 5,336,465 | A | * | 8/1994 | Matsunaga | A61F 2/30767 419/2 |
| 5,397,365 | A | * | 3/1995 | Trentacosta | A61F 2/30965 606/76 |
| 5,480,449 | A | * | 1/1996 | Hamilton | A61F 2/30907 29/465 |
| 5,591,233 | A | * | 1/1997 | Kelman | A61F 2/30965 606/76 |
| 6,800,095 | B1 | * | 10/2004 | Pope | A61F 2/30767 428/212 |
| 6,887,278 | B2 | * | 5/2005 | Lewallen | A61F 2/30767 623/22.11 |
| 6,913,623 | B1 | * | 7/2005 | Zhu | A61F 2/30734 623/23.15 |
| 2003/0114936 | A1 | * | 6/2003 | Sherwood | A61F 2/28 623/23.58 |
| 2003/0155686 | A1 | * | 8/2003 | Hawkins | A61F 2/30907 264/255 |
| 2003/0191533 | A1 | * | 10/2003 | Dixon | A61F 2/30767 623/17.14 |
| 2007/0078521 | A1 | * | 4/2007 | Overholser | A61F 2/30767 623/23.53 |
| 2007/0150068 | A1 | * | 6/2007 | Dong | A61F 2/30767 623/22.32 |
| 2007/0203584 | A1 | * | 8/2007 | Bandyopadhyay | A61F 2/28 623/23.5 |
| 2008/0255675 | A1 | | 10/2008 | Sidebotham | |
| 2008/0262626 | A1 | * | 10/2008 | Raugel | A61F 2/30734 623/22.15 |
| 2009/0182429 | A1 | * | 7/2009 | Humphreys | A61F 2/4425 623/17.16 |
| 2010/0211180 | A1 | * | 8/2010 | Helmuth | C23C 28/048 623/23.5 |
| 2011/0202140 | A1 | * | 8/2011 | Turner | A61F 2/36 623/22.4 |

* cited by examiner

I-I

HIP JOINT DEVICE AND METHOD

This application is the U.S. national phase of International Application No. PCT/SE2010/050816, filed 12 Jul. 2010, which designated the U.S. and claims the benefit of U.S. Provisional Nos.: 61/229,755, filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,735 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900962-2 filed 10 Jul. 2009; 0900963-0 filed 10 Jul. 2009; 0900965-5 filed 10 Jul. 2009; 0900966-3 filed 10 Jul. 2009; 0900968-9 filed 10 Jul. 2009; 0900969-7 filed 10 Jul. 2009; 0900970-5 filed 10 Jul. 2009; 0900972-1 filed 10 Jul. 2009; 0900973-9 filed 10 Jul. 2009; 0900974-7 filed 10 Jul. 2009; 0900976-2 filed 10 Jul. 2009 and 0900978-8 filed 10 Jul. 2009, the entire contents of each of which are hereby incorporated by reference.

TECHNICAL FIELD

The invention relates generally to hip joint prosthesis.

BACKGROUND

Hip joint Osteoarthritis is a syndrome in which low-grade inflammation results in pain in the hip joints, caused by abnormal wearing of the Cartilage acting as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment of hip joint osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed on hundreds of thousand of patients in the world every year. The most common method comprises placing a metal prosthesis in Femur and a plastic bowl in Acetabulum. This operation is done through a lateral incision in the hip and upper thigh and through Fascia Lata and the lateral muscles of the thigh. To get access to the joint, the supporting hip joint capsule attached to Femur and Ilium needs to be penetrated. Femur is then cut at the neck with a bone saw and the prosthesis is placed in femur either with bone cement or without. Acetabulum is slightly enlarged using an Acetabular reamer, and the plastic bowl is positioned using screws or bone cement.

The metal prosthesis placed in femur is normally harder than the human bone which on many occasions injures the femoral bone in the points in which the prosthesis is fixated to the femoral bone. The difference in elasticity between the femoral bone and the hip joint prosthesis also affects the fixation of the prosthesis. Loosening of the prosthesis is the most common reason for needing to redo the hip joint surgery and a difference in elasticity between the prosthesis and the femoral bone creates tension in the fixation points which promotes the loosening of the prosthesis.

An additional problem with having a stiff i.e. not elastic enough prosthesis is that the prosthesis completely takes over the load carrying from the natural bone, which can make the bone retract and decreases its formation of new bone tissue. Eventually this process propagates loosening of the prosthesis. The strain on the contacting surfaces further comes from the shocks propagating through the body from normal walking or more extensive strains in accident situations such as the person falling. A stiff prosthesis does not work in a shock absorbing way and thus the entire shock is propagated to the contacting surface where the prosthesis is fixated to the femoral bone.

It would therefore be desirable to have a hip joint prosthesis with similar elastic properties as the bone in the points that fixates the prosthesis to the bone, and/or to have a hip joint prosthesis that absorbs shocks in a similar or improved way as the natural hip joint.

SUMMARY

A hip joint prosthesis adapted to be implanted in a hip joint of a human patient is provided. The hip joint prosthesis comprises a first area and a second area, said first area comprises a first material or part of material adapted to be elastic and said second area comprises a second material or part of material adapted to be elastic. The first material or part of material is adapted to be more elastic than the second material or part of material.

According to one embodiment the hip joint prosthesis further comprises a first and second end, positioned on a length axis of said hip joint prosthesis. The first end comprises said first material or part of material, and said second end comprises said second material or part of material. A proximal part of said hip joint prosthesis could comprises said first end, and a distal end of said hip joint prosthesis could comprises said second end, when the hip joint prosthesis is implanted in said human patient.

According to one embodiment the hip joint prosthesis is incrementally more elastic from said second end to said first end.

According to another embodiment the hip joint prosthesis further comprises a third, fourth and fifth area, the third area comprises a third material or part of material, the fourth area comprises a fourth material or part of material and the fifth area comprises a fifth material or part of material. The first, second, third, fourth and fifth materials or part of materials could be connected to each other through net attractive forces.

According to one embodiment the first material or part of material is adapted to be more elastic than the second material or part of material and the second material or part of material is adapted to be more elastic than the third material or part of material, the third material or part of material is adapted to be more elastic than the fourth material or part of material, and the fourth material or part of material is adapted to be more elastic than the fifth material or part of material.

According to one embodiment the first material or part of material is adapted to be more elastic than the second material or part of material, the second material is adapted to be more elastic than the third material, the third material or part of material is adapted to be less elastic than the fourth material or part of material, and the fourth material or part of material is adapted to be less elastic than the fifth material or part of material.

According to one embodiment the first material or part of material is adapted to be more elastic than the second material or part of material, the second material is adapted to be more elastic than the third material or part of material, the third material or part of material is adapted to be more elastic than the fourth material or part of material, and the fourth material or part of material is adapted to be less elastic than said fifth material or part of material.

According to one embodiment the first area is the most proximal area of said first, second, third, fourth and fifth areas, the second area is the second most proximal area of said first, second, third, fourth and fifth areas, the third area is the third most proximal of said first, second, third, fourth and fifth areas, the fourth area is the fourth most proximal of said first, second, third, fourth and fifth areas, and the fifth area is the fifth most proximal of said first, second, third, fourth and fifth areas, when said hip joint prosthesis is implanted is said human patient.

According to one embodiment the first material or part of material is adapted to be more elastic than the second material or part of material, the second material or part of material is adapted to be more elastic than the third material or part of material, the third material or part of material is adapted to be more elastic than the fourth material or part of material, and the fourth material or part of material is adapted to be more elastic than the fifth material or part of material.

According to one embodiment the first material or part of material is adapted to be more elastic than said second material or part of material, the second material or part of material is adapted to be more elastic than said third material or part of material, the third material or part of material is adapted to be less elastic than said fourth material or part of material, and the fourth material or part of material is adapted to be less elastic than said fifth material or part of material.

According to one embodiment the first material or part of material is adapted to be more elastic than the second material or part of material, the second material or part of material is adapted to be more elastic than said third material or part of material, the third material or part of material is adapted to be more elastic than said fourth material or part of material, and the fourth material or part of material is adapted to be less elastic than said fifth material or part of material.

According to one embodiment the first, second, third, fourth and fifth materials or part of materials all comprises different materials in any combination or different parts of the same material, wherein all materials or different parts of said materials all have different elasticity.

The hip joint further comprises an acetabulum being a bowl shaped part of the pelvic bone. The hip joint prosthesis could further comprise a connection section, comprising a connection surface. The connection surface comprises a first surface material or part of material having an average elasticity, wherein said surface is adapted to be in connection with the acetabulum, or an artificial replacement therefor. The hip joint prosthesis could further comprise a fixating section comprising a fixating surface. The fixating surface comprising a second surface material or part of material having an average elasticity adapted to assist in the fixation of said hip joint prosthesis to the femoral bone of said human patient.

According to one embodiment the average elasticity of the first surface material or part of material is lower than the average elasticity of said second surface material or part of material.

Material

According to one embodiment the hip joint prosthesis comprises metal, which could be a metal alloy, which in turn could comprise steel and/or a biocompatible metal.

According to one embodiment the percentage of Martensite is higher in said first surface material or part of material than in said second surface material or part of material.

It is also conceivable that said hip joint prosthesis comprises a polymer material.

In the embodiments where the hip joint prosthesis comprises a firs and a second material or part of material it is conceivable that both said firs and said second material or part of material comprises metal. The metal materials or part of material could be a metal selected from a group consisting of: steel, steel alloys, titanium, titanium alloys and biocompatible metal. In the embodiments where the hip joint prosthesis comprises a first, second, third, fourth and fifth material or part of material it is conceivable that all of said first, second, third, fourth and fifth materials or part of materials are metal materials, which in turn could be a metal selected from a group consisting of: steel, alloys comprising steel, titanium, titanium alloys and biocompatible metal.

Fixating Section

According to one embodiment the hip joint prosthesis is adapted to be fixated to the collum femur. In which case the prosthesis could be adapted to be fixated to the collum femur on the inside thereof. In other embodiments the hip joint prosthesis is adapted to be fixated to the femoral bone, in which case it could be adapted to be fixated to the inside thereof.

Connecting Section

According to one embodiment the connecting section comprises a ceramic material or part of material, which could be titanium carbide.

Material Connected Through Net Attractive Forces

According to one embodiment the hip joint prosthesis comprises a first area and a second area, connected to each other through net attractive forces. The first area comprises a first material or part of material adapted to be elastic and said second area comprises a second material or part of material adapted to be elastic, and the first material or part of material is adapted to be more elastic than said second material or part of material.

According to one embodiment the hip joint prosthesis further comprises a first and second end, positioned on a length axis of said hip joint prosthesis. The first end comprises the first material or part of material, and the second end comprises the second material or part of material.

According to one embodiment a proximal part of the hip joint prosthesis comprises said first end, and a distal end of said hip joint prosthesis comprises said second end, when said hip joint prosthesis is implanted in said human patient. It is also conceivable that the hip joint prosthesis is incrementally more elastic from said second end to said first end.

According to one embodiment the hip joint prosthesis further comprises a third, fourth and fifth area. The third area comprises a third material or part of material, the fourth area comprises a fourth material or part of material, the fifth area comprises a fifth material or part of material. The first, second, third, fourth and fifth materials or part of materials are connected to each other through net attractive forces.

According to one embodiment the first material or part of material is adapted to be more elastic than the second material or part of material, the second material or part of material is adapted to be more elastic than the third material or part of material, the third material or part of material is adapted to be more elastic than the fourth material or part of material, and the fourth material or part of material is adapted to be more elastic than the fifth material or part of material.

According to another embodiment the first material or part of material is adapted to be more elastic than said second material or part of material, the second material or part of material is adapted to be more elastic than said third material or part of material, the third material or part of material is adapted to be less elastic than said fourth material or part of material, and the fourth material or part of material or part of material is adapted to be less elastic than the fifth material or part of material.

According to another embodiment the first material or part of material is adapted to be more elastic than said second material or part of material, the second material or part of material is adapted to be more elastic than said third material or part of material, the third material or part of material is adapted to be more elastic than said fourth material or part of material, and the fourth material or part of material is adapted to be less elastic than said fifth material or part of material.

According to one embodiment the first area is the most proximal area of said first, second, third, fourth and fifth areas, the second area is the second most proximal area of said first, second, third, fourth and fifth areas, the third area is the third most proximal of said first, second, third, fourth and fifth areas, the fourth area is the fourth most proximal of said first, second, third, fourth and fifth areas, the fifth area is the fifth most proximal of said first, second, third, fourth and fifth areas, when said hip joint prosthesis is implanted is said human patient.

According to one embodiment the first material or part of material is adapted to be more elastic than said second material or part of material, the second material or part of material is adapted to be more elastic than said third material or part of material, the third material or part of material is adapted to be more elastic than said fourth material or part of material, and the fourth material or part of material is adapted to be more elastic than said fifth material or part of material.

According to one embodiment the first material or part of material is adapted to be more elastic than the second material or part of material, the second material or part of material is adapted to be more elastic than said third material or part of material, the third material or part of material is adapted to be less elastic than said fourth material or part of material, and the fourth material or part of material is adapted to be less elastic than said fifth material or part of material.

According to one embodiment the first material or part of material is adapted to be more elastic than said second material or part of material, the second material or part of material is adapted to be more elastic than said third material or part of material, the third material or part of material is adapted to be more elastic than said fourth material or part of material, and the fourth material or part of material is adapted to be less elastic than said fifth material or part of material.

The hip joint of a human patient comprises an acetabulum, being a bowl shaped part of the pelvic bone. The hip joint prosthesis according to any of the embodiments could furthermore comprise a connection section comprising a connection surface. The connection surface comprising a first surface material or part of material having an average elasticity, and wherein said surface is adapted to be in connection with said acetabulum, or an artificial replacement therefor. The prosthesis further comprises a fixating section comprising a fixating surface. The fixating surface comprises a second surface material or part of material having an average elasticity, adapted to assist in the fixation of said hip joint prosthesis to the femoral bone of said human patient.

According to one embodiment the average elasticity of said first surface material or part of material is lower than said average elasticity of said second surface material or part of material.

Material

According to one embodiment the hip joint prosthesis comprises metal, such as a metal alloy, which in turn could comprise steel, a biocompatible metal.

According to one embodiment the percentage of Martensite is higher in said first surface material than in said second surface material.

According to one embodiment the hip joint prosthesis comprises a polymer material.

In the embodiments where the hip joint prosthesis comprises a first and second material, it is conceivable that the first and second materials are metal materials. The metal material could comprise a metal selected from a group consisting of: steel, steel alloys, titanium, titanium alloys and biocompatible metal.

According to other embodiments a first, second, third, fourth and fifth materials could be metal materials, which in turn could comprise a metal selected from a group consisting of: steel, steel alloys, titanium, titanium alloys and biocompatible metal.

Fixating Section

According to one embodiment the hip joint prosthesis is adapted to be fixated to the collum femur, said fixation could be done from the inside thereof.

According to another embodiment the hip joint prosthesis is adapted to be fixated to the femoral bone, said fixation could be done from the inside thereof. A combination of the mentioned alternatives is also conceivable.

Connecting Section

According to one embodiment the connecting section comprises a ceramic material such as titanium carbide. It is also conceivable that the material of the connecting section is a porous material.

Bending and Twisting

The hip joint prosthesis could comprise a fixating section, a connecting section and an intermediary section placed between the fixating section and the connecting section. The hip joint prosthesis according to ay of the embodiments could be adapted to deform elastically when exposed to a force through the intermediary section being adapted to bend to a curvature when exposed to a force, or to deform elastically when exposed to a force through said intermediary section being adapted to twist when exposed to a force, or to deform elastically when exposed to a force through said intermediary section being adapted to bend to a curvature and twist when exposed to a force.

According to one embodiment the intermediary section is adapted to bend to a curvature with $\kappa>2$, according to another embodiment the intermediary section is adapted to bend to a curvature with $\kappa>4$ and according to yet another embodiment the intermediary section is adapted to bend to a curvature with $\kappa>8$, all while the fixating section remains fixedly attached to the femoral bone.

According to one embodiment the intermediary section is adapted to twist till the angle of twist $(\varphi)>0.005\pi$ while the fixating section remains fixedly attached to the femoral bone, according to another embodiment the intermediary section is adapted to twist till the angle of twist $(\varphi)>0.01\pi$, and according to yet another embodiment the intermediary section is adapted to twist till the angle of twist $(\varphi){>}0.02\pi$ while the fixating section remains fixedly attached to the femoral bone. It is also conceivable that the intermediary section is adapted to bend to a curvature with $\kappa{>}2$, and twist till the angle of twist $(\varphi){>}0.005\pi$ while the fixating section remains fixedly attached to the femoral bone.

Method

A method of absorbing a force in the hip joint of a human patient using the hip joint prosthesis according to any of the embodiments is further provided. The method comprises the step of said hip joint prosthesis deforming elastically, which comprises the steps of: the material of said first area of said hip joint prosthesis deforming elastically, when exposed to a force, and the material of the second area of the hip joint prosthesis deforming less elastically than the material of the first area of the hip joint prosthesis, when exposed to the force.

According to one embodiment, the step of the material of the first area of the hip joint prosthesis deforming elastically when exposed to a force, comprises the step of said material deforming more elastically than the material of the femoral bone, and the step of the material of the second area of the hip joint prosthesis deforming less elastically than said material of said first area of said hip joint prosthesis when exposed to a force, comprises the step of the material deforming substantially equally elastically as the material of the femoral bone.

According to yet another embodiment the step of the material of the first area of the hip joint prosthesis deforming elastically when exposed to a force, comprises the step of the material deforming more elastically than the material of the femoral bone, and wherein the step of the material of the second area of the hip joint prosthesis deforming less elastically than the material of the first area of the hip joint prosthesis when exposed to a force, comprises the step of the material deforming substantially equally elastically as the bone cement used to fixate the hip joint prosthesis to the femoral bone.

According to one embodiment, the hip joint prosthesis comprises a fixating section, a connecting section and an intermediary section placed between the fixating section and the connecting section. The step of the hip joint prosthesis deforming elastically when exposed to a force could comprise the step of the intermediary section bending to a curvature when exposed to a force, or the intermediary section twisting when exposed to a force, or the intermediary section bending and twisting when exposed to a force, while the fixating section remaining fixedly attached to the femoral bone, and the femoral bone remaining intact.

According to one embodiment the intermediary section bends to a curvature with $\kappa{>}2$, according to another embodiment the intermediary section bends to a curvature with $\kappa{>}4$ and according to yet another embodiment the intermediary section bends to a curvature with $\kappa{>}8$, all while the fixating section remains fixedly attached to the femoral bone.

According to one embodiment the intermediary section twists till the angle of twist $(\varphi){>}0.005\pi$ while the fixating section remains fixedly attached to the femoral bone, according to another embodiment the intermediary section twists till the angle of twist $(\varphi){>}0.01\pi$, and according to yet another embodiment the intermediary section twists till the angle of twist $(\varphi){>}0.02\pi$ while the fixating section remains fixedly attached to the femoral bone. It is also conceivable that the intermediary section bends to a curvature with $\kappa{>}2$, and twists till the angle of twist $(\varphi){>}0.005\pi$ while the fixating section remains fixedly attached to the femoral bone. It is also conceivable that the intermediary section bends to a curvature with $\kappa{>}2$, and twists till the angle of twist $(\varphi){>}0.005\pi$ while the fixating section remains fixedly attached to the femoral bone.

According to one embodiment, the proximal part of the hip joint prosthesis comprises said first end, and wherein a distal end of said hip joint prosthesis comprises said second end, when implanted, and wherein said hip joint prosthesis further has on top a hard less elastic layer at the surface of the first end.

According to one embodiment, below/distally to the top hard less elastic layer at the surface of the first end, the prosthesis is substantially more elastic and further distally incrementally less elastic in distal direction.

According to one embodiment, the part of the prosthesis being further distally incrementally less elastic in distal direction, is ending distally where the prosthesis first contacts the femoral bone, when implanted.

According to one embodiment, the part of the prosthesis placed in the femoral bone being further distally incrementally more elastic in distal direction, when implanted.

According to one embodiment, the part of the prosthesis placed in the femoral bone having a elasticity close to the elasticity of the bone.

Please note that any embodiment or part of embodiment as well as any method or part of method could be combined in any way.

BRIEF DESCRIPTION OF DRAWINGS

Embodiments now described, by way of example, with reference to the accompanying drawings, in which.

DETAILED DESCRIPTION

Figure 1:
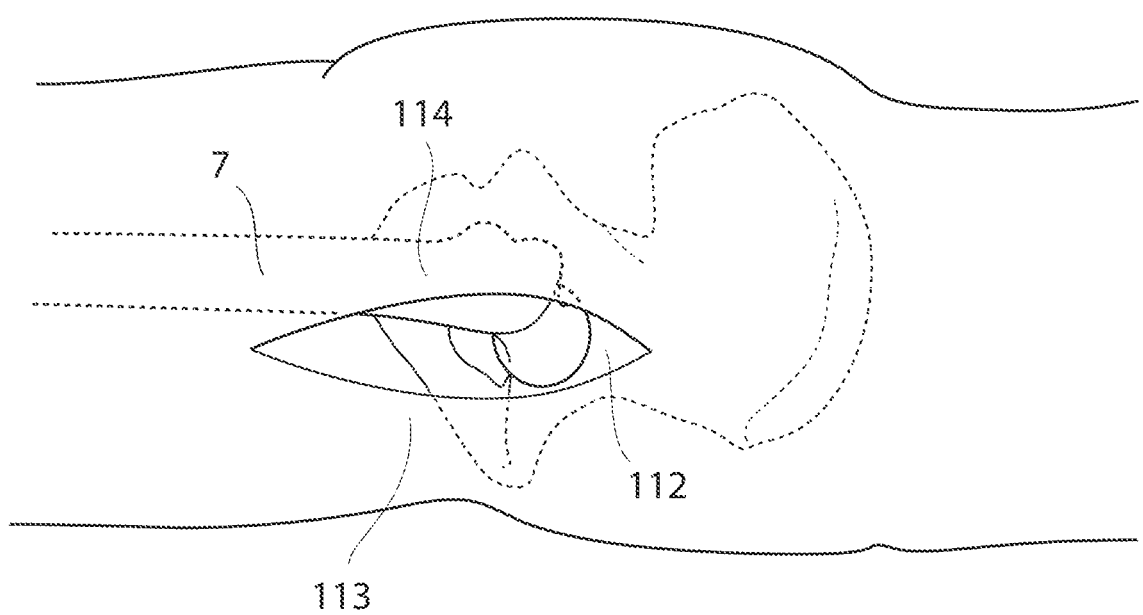
FIG. 1 shows a human patient in a lateral view, when a conventional hip joint surgery is performed.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

Net attractive forces is to be understood as; that the materials which are connected to each other through attractive forces on a atomic or molecular level. These net attractive forces could be van der Waals forces, bipolar forces or covalent forces. The material connected through net attractive forces could be the same material, the same base material with different treatments or different materials fixated to each other through some sort of binding force.

The proximal part of the hip joint prosthesis is to be understood as the part being located proximally in a human patient when implanted. The proximal part is thus the part comprising the connection section in connection with the acetabulum. The distal part is the part of the prosthesis being located distally in a human patient when implanted. The distal part comprises the fixation section adapted to fixate the prosthesis to the femoral bone and/or the collum femur.

Part of a material is to be understood as a part or section of a material which does not necessarily have the same properties as the other parts of the same material, e.g. a part of a metal material can be hardened differently from another part of the metal material even if the two parts are parts of the same base material, this is analogous for polymer and ceramic materials.

Biocompatible material is to be understood as being a material with low level of immune response. Biocompatible materials are sometimes also referred to as biomaterials. Analogous is biocompatible metals a biocompatible metal with low immune response such as titanium or tantalum. The biocompatible metal could also be a biocompatible alloy comprising at least one biocompatible metal.

A metal alloy is to be understood as a mixture of two or more elements in solid solution in which the major component is a metal. A steel alloy is hence an alloy wherein one of the components is steel which in turn is an alloy of iron and carbon. A titanium alloy is hence an alloy wherein one of the components is titanium.

Martensite is a very hard form of steel crystalline structure, but it is also any crystal structure that is formed by displacive transformation. It includes a class of hard minerals occurring as lath- or plate-shaped crystal grains.

According to one embodiment the hip joint prosthesis is a steel alloy prosthesis, such as a stainless steel prosthesis, wherein one of the ends of the prosthesis is adapted to be in connection with the acetabulum, which is a bowl shaped part of the pelvic bone. The connection section has a less elastic surface adapted to better resist wearing than the rest of the prosthesis. The less elastic surface is formed through quenching of the surface, which is a process wherein said surface is rapidly heated and then rapidly cooled. The quenching creates Martensite in the surface by not allowing carbon atoms to diffuse out of the crystal structure. The prosthesis further comprises a fixating section which assists in the fixation of the prosthesis to the femoral bone. The fixating section could be only the parts of the prosthesis having a surface which is in direct or indirect connection with the femoral bone, in which case the prosthesis further comprises and intermediary section adapted to be located between said connection section and said fixation section. According to another embodiment the fixating section is all of the prosthesis apart from the connection section. The connection section could be quenched by rapidly cooling that particular part, it is however also conceivable that the entire prosthesis is quenched and that the sections which are not exposed to any wearing are tempered to create a more elastic structure in the material.

According to one embodiment the connection section and the fixation section is a biocompatible metal material, whereas the intermediary section is a biocompatible polymer material such as polyurethane elastomeric materials, polyamide elastomeric materials, polyester elastomeric materials and silicone materials.

According to one embodiment the hip joint prosthesis is a titanium or titanium alloy prosthesis in which the connection section comprises a ceramic layer such as titanium carbide to create a more wear resistant surface. The titanium or titanium alloy prosthesis could be tempered to create a more elastic structure in the material.

The medical device according to any of the embodiments could comprise at least one material selected from a group consisting of: polytetrafluoroethylene (PTFE), perfluoro-alkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows a lateral view of a conventional hip joint surgery where an incision 112 is made in the tight 113 enabling the surgeon to reach the femoral bone 7 on which the caput femur 5 is located. In a conventional hip joint surgery the hip joint is accessed through the hip joint capsule, which forces the surgeon to penetrate the tissue of the capsule.

Figure 2:
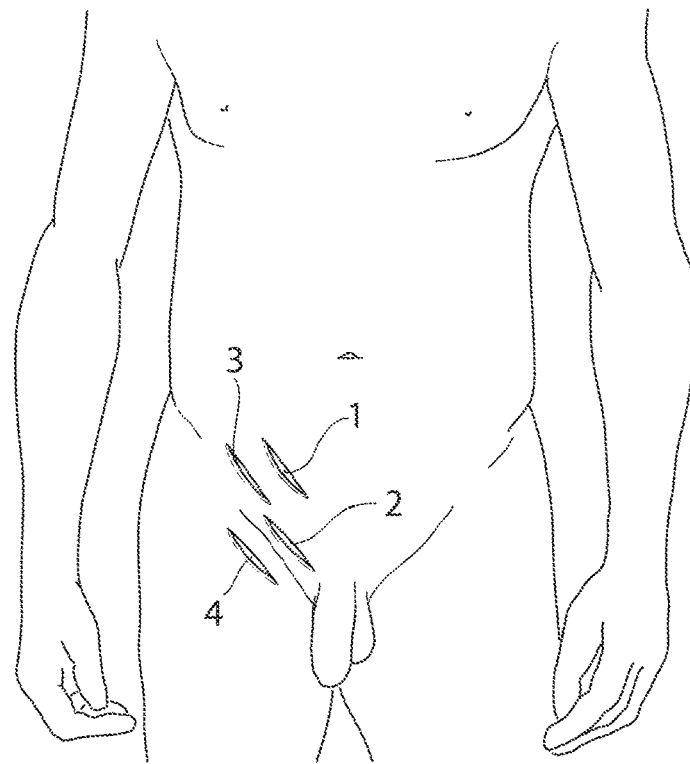
FIG. 2 shows a frontal view of a human patient when incisions have been made in a surgical method.

FIG. 2 shows a frontal view of the body of a human patient where a surgical method of providing a hip joint prosthesis from the opposite side from acetabulum is performed. The method is, according to a first embodiment, performed starting with an incision 1 in the abdominal wall of the human patient. The incision 1 passes through the rectus abdominis and peritoneum, in to the abdomen of the human patient. In a second embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9.

Figure 3:
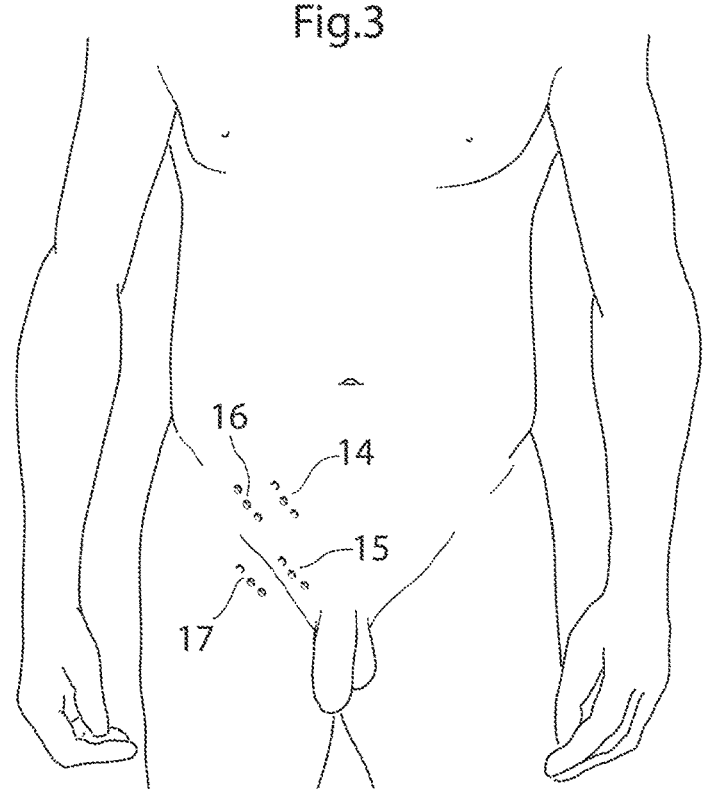
FIG. 3 shows a frontal view of a human patient when incisions have been made in a laparoscopic method.

FIG. 3 shows a frontal view of the body of a human patient where a laparoscopic method of providing a hip joint prosthesis from the opposite side from acetabulum is performed. The method is according to a first embodiment performed starting with making small incisions 14 in the abdominal wall of the human patient. The small incisions enable the surgeon to insert laparoscopic trocars into the abdomen of the human patient. According to the first embodiment the incisions 14 passes through the abdominal wall and peritoneum, in to the abdomen of the human patient. According to a second embodiment the small incisions 15 is conducted through the abdominal wall, preferably rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 4:
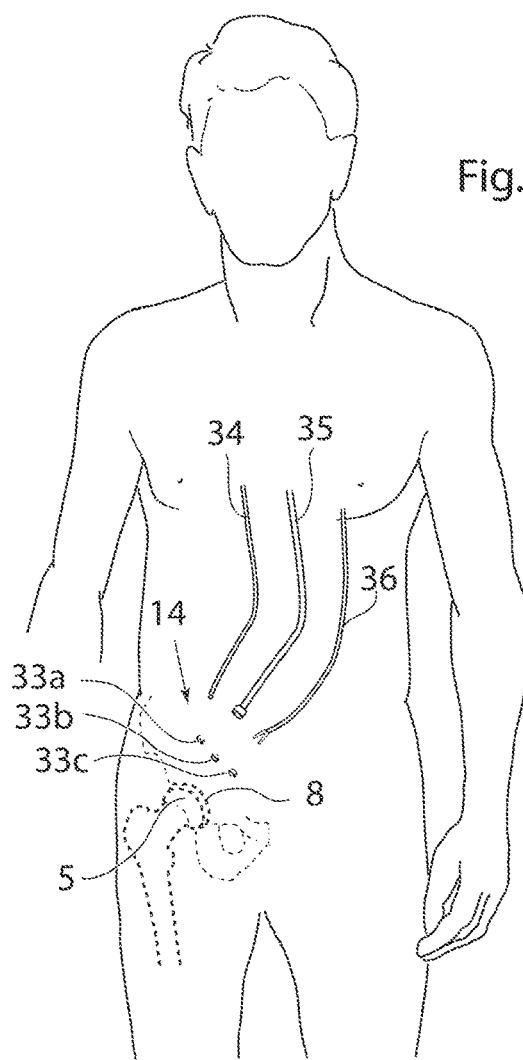
FIG. 4 shows a frontal view of a human patient and the tools of a laparoscopic method.

FIG. 4 shows a frontal view of the body of a human patient, illustrating the laparoscopic method of operating the hip joint from the opposite side from acetabulum 8. The hip joint comprises the acetabulum 8 and the caput femur 5. The small incisions 14 in the abdominal wall of the human patient allows the insertion of laparoscopic trocars 33a,b,c into the body of the patient. Whereafter one or more camera 34, a surgical instrument adapted to create a hole in the pelvic bone 35, or instruments 36 for introducing, placing, connecting, attaching, creating or filling prosthesis or prosthetic parts, can be inserted into said body through said laparoscopic trocars 33a,b,c.

Figure 5:
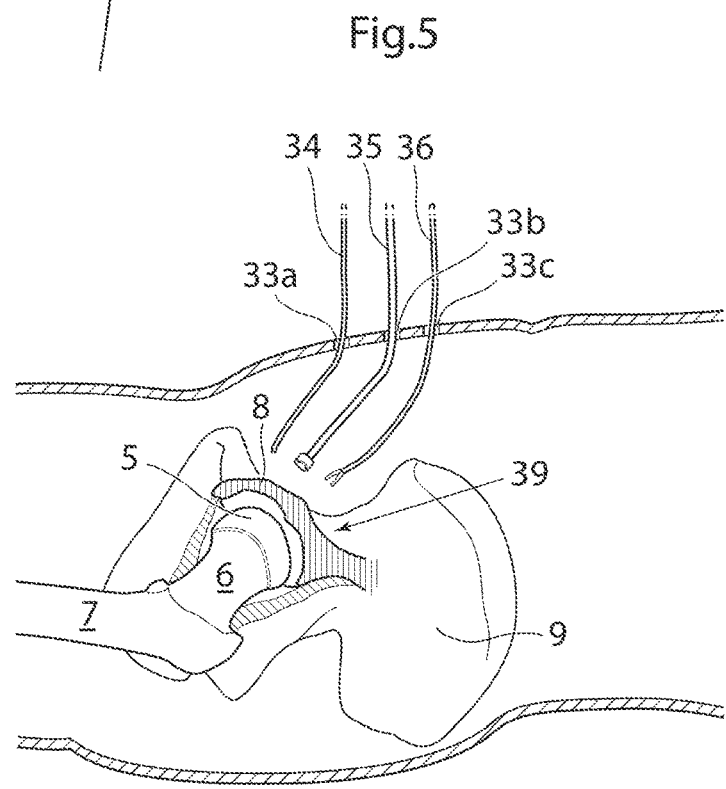
FIG. 5 shows a human patient in section when a laparoscopic method is performed.

FIG. 5 shows a lateral view of the body of a human patient, with the hip joint shown in section in further detail. The hip joint comprises a caput femur 5 placed at the very top of collum femur 6 which is the top part of the femoral bone 7. The caput femur is in connection with the acetabulum 8 which is a bowl shaped part of the pelvic bone 9. Laparoscopic trocars 33a,b,c is being used to reach the hip joint 39 with one or more camera 34, a surgical instrument adapted to create a hole in the pelvic bone 35, or instruments 36 for introducing, placing, connecting, attaching, creating or filling prosthesis or prosthetic parts.

Figure 6:
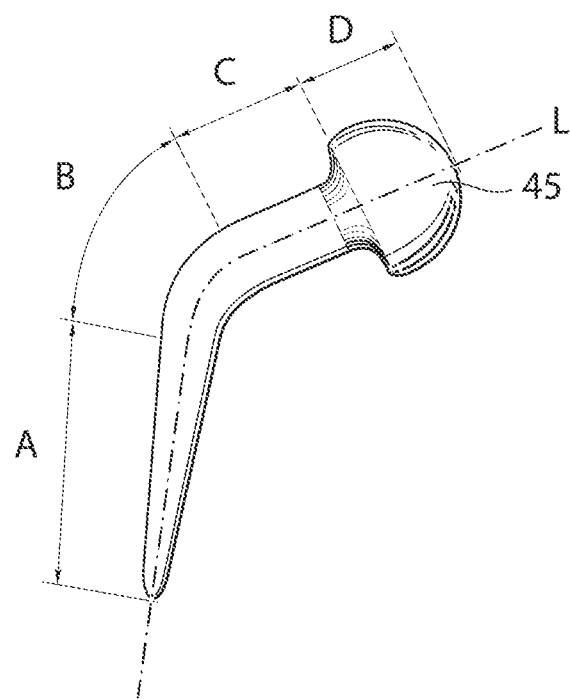
FIG. 6 shows the hip joint prosthesis according to one embodiment.

FIG. 6 shows the hip joint prosthesis according to an embodiment where the hip joint prosthesis is adapted to be fixated to the femoral bone by means of a fixating section A. The hip joint prosthesis is adapted to have sections, which are schematically denoted A,B,C and D, said section is adapted to have different properties. According to one embodiment section A is adapted to be less elastic than section B, which in turn is adapted to be less elastic than section C, which in turn is adapted to be less elastic than section D. This enables the first section A to be securely fixated to the femoral bone at the same time as the hip joint prosthesis, through the more elastic sections, is able to absorb shocks created by the movements and loads from the human patient. According to another embodiment section A is adapted to be less elastic than section B, which in turn is adapted to be less elastic than section C but more elastic than section D. This enables the first section A to be securely fixated to the femoral bone, the hip joint prosthesis to absorb shocks, at the same time as the connecting section D can resist the wear created by the contact with the acetabulum 8 or artificial replacement therefor. However, it is also conceivable, in any of the embodiments that the artificial caput femur surface 45 comprises a surface material adapted to resist wear, which could be a less elastic metal material, a ceramic material, a carbon material or a polymer material.

Figure 7:
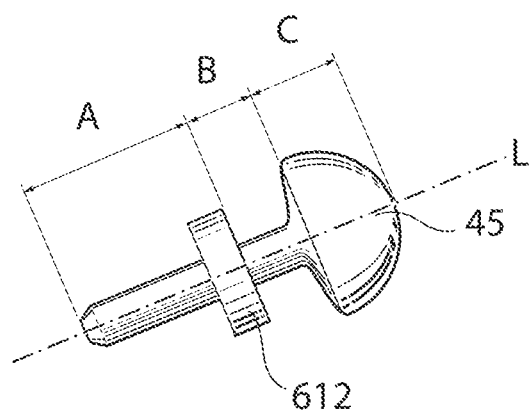
FIG. 7 shows the hip joint prosthesis according to one embodiment.

FIG. 7 shows the hip joint prosthesis according to an embodiment where the hip joint prosthesis is adapted to be fixated to the collum femur by means of a fixating section A. The hip joint prosthesis comprises three sections schematically denoted A, B and C. According to one embodiment, section A is adapted to be less elastic than section B, which in turn in less elastic than section C. This enables the first section A to be securely fixated to the collum femur, at the same time as the hip joint prosthesis, through the more elastic sections, is able to absorb shocks created by the movements and loads from the human patient. According to one embodiment, section A is less elastic than section B, which in turn is more elastic than section C. This enables the first section A to be securely fixated to the collum femur, the hip joint prosthesis to absorb shocks, at the same time as the connecting section C can resist the wear created by the contact with the acetabulum 8 or artificial replacement therefor. However, it is also conceivable, in any of the embodiments that the artificial caput femur surface 45 comprises a surface material adapted to resist wear, which could be a less elastic metal material, a ceramic material, a carbon material or a polymer material.

Figure 8:
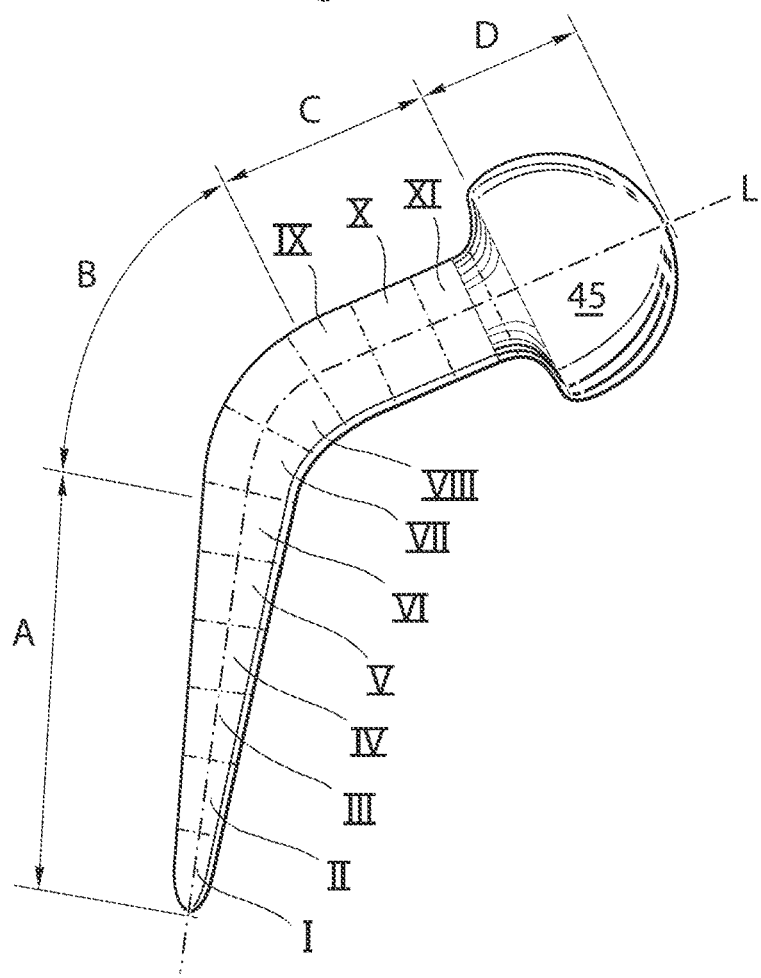
FIG. 8 shows the hip joint prosthesis according to one embodiment, in further detail.

FIG. 8 shows the hip joint prosthesis in one embodiment where the hip joint prosthesis comprises several sections, schematically denoted I-XI. According to this embodiment the hip joint prosthesis is made of a metallic material, which is hardened so that the different sections have different properties. The hardening process can be performed in a way so that there are clear sections with different properties, however it is also conceivable that said different properties are propagates the hip joint prosthesis continuously i.e. there are no clear boarders, rather continuously varying properties throughout the hip joint prosthesis. However the hip joint prosthesis comprises sections adapted for different operational purposes. The fixating section A preferably comprises sections of the sections I-XI which are less elastic since the ability to securely fixate the hip joint prosthesis to the femoral bone is assisted by the hip joint prosthesis not dramatically changing shape. The sections B and C preferably comprises sections of the sections I-XI which are more elastic since this part of the hip joint prosthesis could change its shape without that having any dramatic effect on the mechanical function of the hip joint prosthesis. The connecting section D comprising the artificial caput femur surface 45 preferably comprises either a section of the metal material adapted to be less elastic and more resistant to wear, or a surface material separated from the rest of the hip joint prosthesis and adapted to resist the wear created by the connection with the acetabulum or artificial replacement therefor. According to other embodiments the material is a polymer material hardened or stretched to create different properties in the different sections of the hip joint prosthesis. According to other embodiments the hip joint prosthesis is made of ceramic or powder based material, in which case the hip joint prosthesis can be hardened or sintered to produce different properties in the different sections extending along a length axis L of the hip joint prosthesis.

Figure 9:
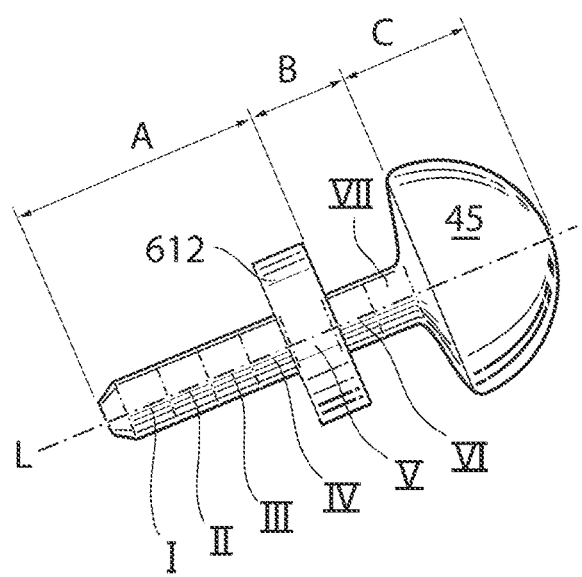
FIG. 9 shows the hip joint prosthesis according to one embodiment, in further detail.

FIG. 9 shows the hip joint prosthesis in one embodiment where the hip joint prosthesis comprises several sections, schematically denoted I-VII. According to this embodiment the hip joint prosthesis is made of a metallic material, which is hardened so that the different sections have different properties. The hardening process can be performed in a way so that there are clear sections with different properties, however it is also conceivable that said different properties propagates the hip joint prosthesis continuously i.e. there are no clear boarders, rather continuously varying properties throughout the hip joint prosthesis. However the hip joint prosthesis comprises sections adapted for different operational purposes. The fixating section A preferably comprises sections of the sections I-VII which are less elastic since the ability to securely fixate the hip joint prosthesis to the collum femur 6 is assisted by the hip joint prosthesis not dramatically changing shape. The section B preferably comprises sections of the sections I-VII which are more elastic since this part of the hip joint prosthesis could change its shape without that having any dramatic effect of the mechanical function of the hip joint prosthesis. The connecting section C comprising the artificial caput femur surface 45 preferably comprises either a section of the metal material adapted to be less elastic and more resistant to wear, or a surface material separated from the rest of the hip joint prosthesis and adapted to resist the wear created by the connection with the acetabulum, or artificial replacement therefor. According to other embodiments the material is a polymer material hardened or stretched to create different properties in the different sections of the hip joint prosthesis. According to other embodiments the hip joint prosthesis is made of ceramic or powder based material, in which case the hip joint prosthesis can be hardened or sintered to produce different properties in the different sections extending along a length axis L of the hip joint prosthesis.

Figure 10:
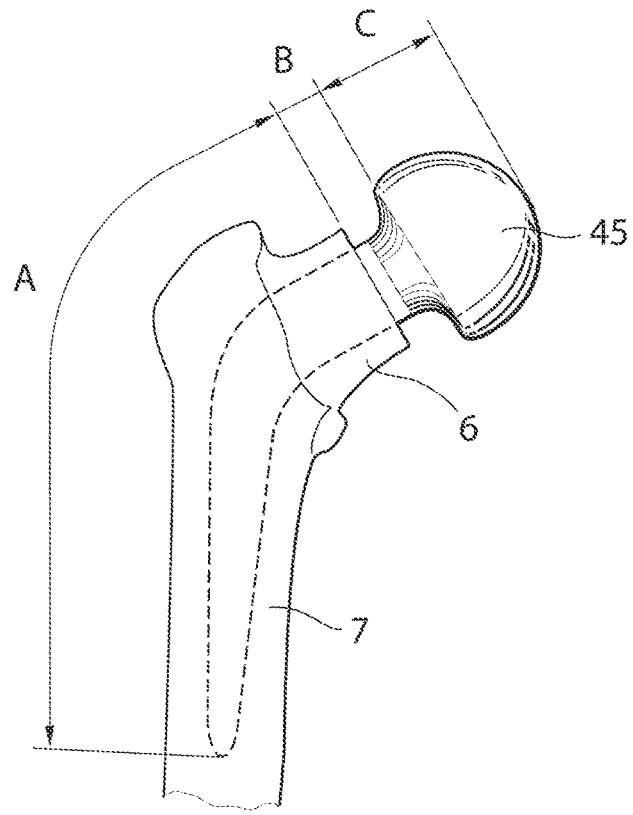
FIG. 10 shows the hip joint prosthesis according to one embodiment, when fixated in the femoral bone.

FIG. 10 shows the hip joint prosthesis when fixated to the femoral bone 7. According to this embodiment the hip joint prosthesis is adapted to be fixated to both the femoral bone 7 and the collum femur 6. According to this embodiment the fixating section A of the hip joint prosthesis comprises the majority of the hip joint prosthesis, whereas the part B, adapted to be more elastic to absorb shocks and vibrations created by the movement of the human patient is substantially shorter as seen in the figure.

Figure 11:
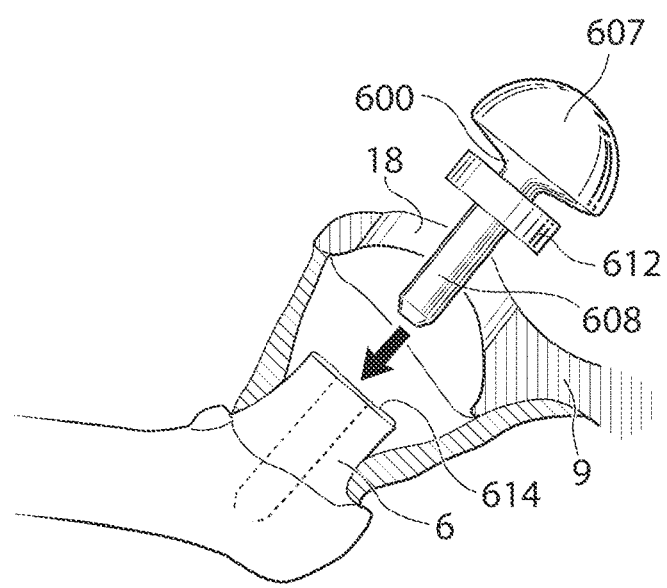
FIG. 11 shows the hip joint prosthesis according to one embodiment, when fixated in the collum femur.

FIG. 11 shows the hip joint in section in an embodiment where the hip joint prosthesis adapted to be fixated to the collum femur, in accordance with embodiments above, is adapted to be placed in the hip joint through a hole 18 in the pelvic bone 9. According to this embodiment the hip joint prosthesis comprises a supporting member 612 which supports the hip joint prosthesis from the outside of the collum femur 6, and from the acetabulum side of the collum femur 6 through the connection with the surface of the section 614 of the collum femur 6.

Figure 12:
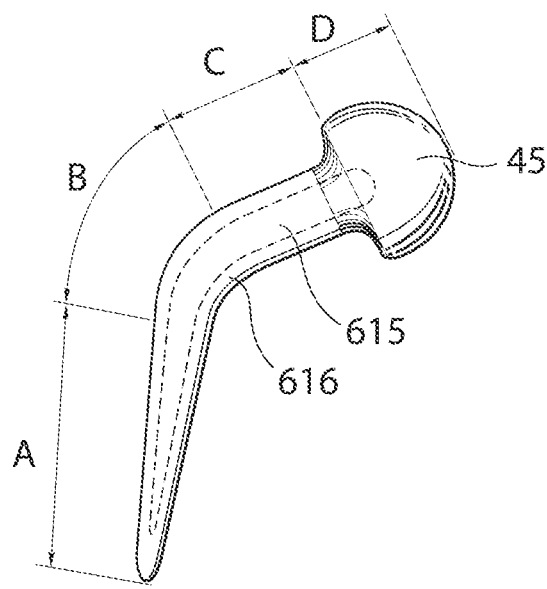
FIG. 12 shows the hip joint prosthesis according to one embodiment.

FIG. 12 shows the hip joint prosthesis according to an embodiment where the hip joint prosthesis comprises a less elastic core structure 615 and a more elastic surface structure 616. The hip joint prosthesis could be made of a metallic material adapted to be hardened in different steps or from the outside and in so that the core section 615 and the surface structure gets different properties. It is furthermore possible to vary the thickness of the surface sections along the prolongation of the hip joint prosthesis such that for example the fixating section A, adapted to fixate the hip joint prosthesis to the femoral bone 7, comprises a relatively larger portion of the less elastic core material 615 which assists the fixation of the hip joint prosthesis in the femoral bone. In the same way, the sections B and C which preferably could be adapted to be more elastic to enable those sections to absorb shocks and vibrations created by the movements of the human patient. The hip joint prosthesis could be separated in a more elastic surface section 616 and a less elastic core section by means of clearly defined sections, however it is also conceivable that this separation is done in a continuous way i.e. there are no clear boarders between the core section 615 and the surface section 616.

Figure 13:
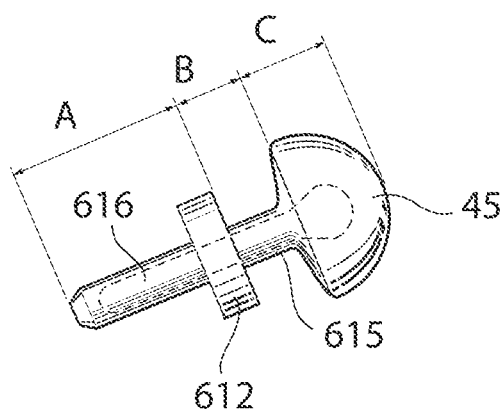
FIG. 13 shows the hip joint prosthesis according to one embodiment.

FIG. 13 shows the hip joint prosthesis according to an embodiment where the hip joint prosthesis comprises a less elastic core structure 615 and a more elastic surface structure 616. The hip joint prosthesis could be made of a metallic material adapted to be hardened in different steps or from the outside and in so that the core section 615 and the surface structure gets different properties. It is furthermore possible to vary the thickness of the surface sections along the prolongation of the hip joint prosthesis such that for example the fixating section A, adapted to fixate the hip joint prosthesis to the collum femur 6, comprises a relatively larger portion of the less elastic core material 615 which assists the fixation of the hip joint prosthesis in the femoral bone. In the same way, the sections B and C which preferably could be adapted to be more elastic to enable those sections to absorb shocks and vibrations created by the movements of the human patient. The hip joint prosthesis could be separated in a more elastic surface section 616 and a less elastic core section by means of clearly defined sections, however it is also conceivable that this separation is done in a continuous way i.e. there are no clear boarders between the core section 615 and the surface section 616.

Figure 14:
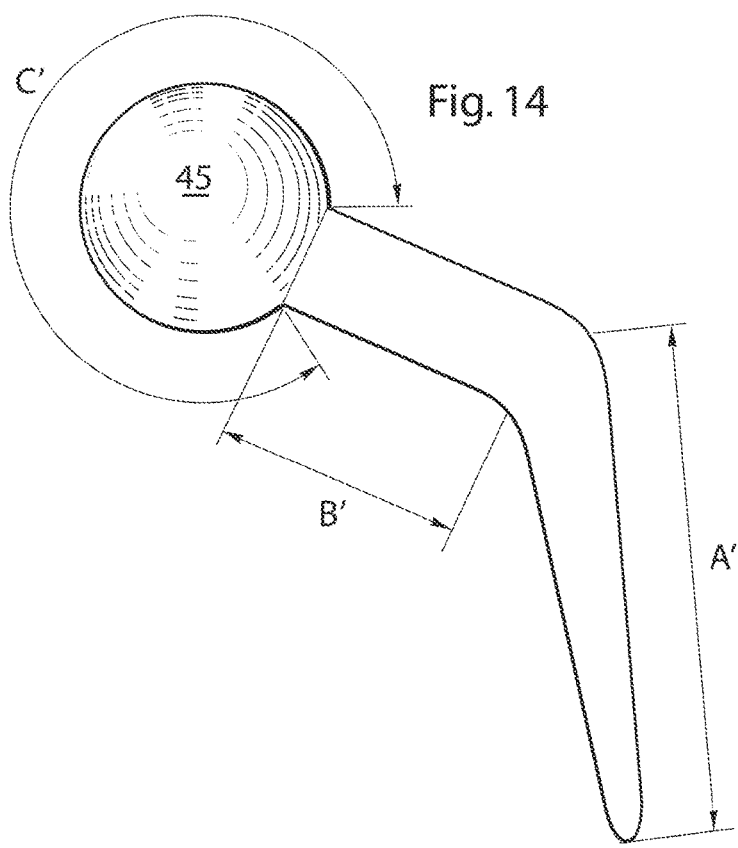
FIG. 14 shows the hip joint prosthesis and its different portions.

FIG. 14 shows an embodiment of the hip joint prosthesis in which the hip joint prosthesis comprises a fixating section A', a connecting section C', extending around the circumference of the artificial caput femur part 45 of the hip joint prosthesis, and an intermediary section B' positioned between said fixating section A' and said connecting section C'. The fixating section is adapted to be fixated to the femoral bone, on the inside thereof. For moving together in conjunction with the femoral bone and thereby reducing the risk of fracture of the femoral bone or loosening of the prosthesis, the fixating section A' could be made of a material with similar elasticity as the femoral bone and/or the bone cement used to fixate the hip joint prosthesis to the femoral bone. According to one embodiment the connecting section C' comprises a surface material being less elastic than the core material of the connecting section C' for better resisting wear against the acetabulum, or an artificial replacement therefor. It is generally conceivable that the fixating section A', the connecting section C' and the intermediary section B' could comprise materials, or parts of materials having different modulus of elasticity. It is also conceivable that the hip joint prosthesis comprises different materials within one section, varying in the prolongation thereof, and/or perpendicularly to the prolongation, e.g. as a core of the hip joint prosthesis having one elasticity and a surface of the hip joint prosthesis having one elasticity.

Figure 15:
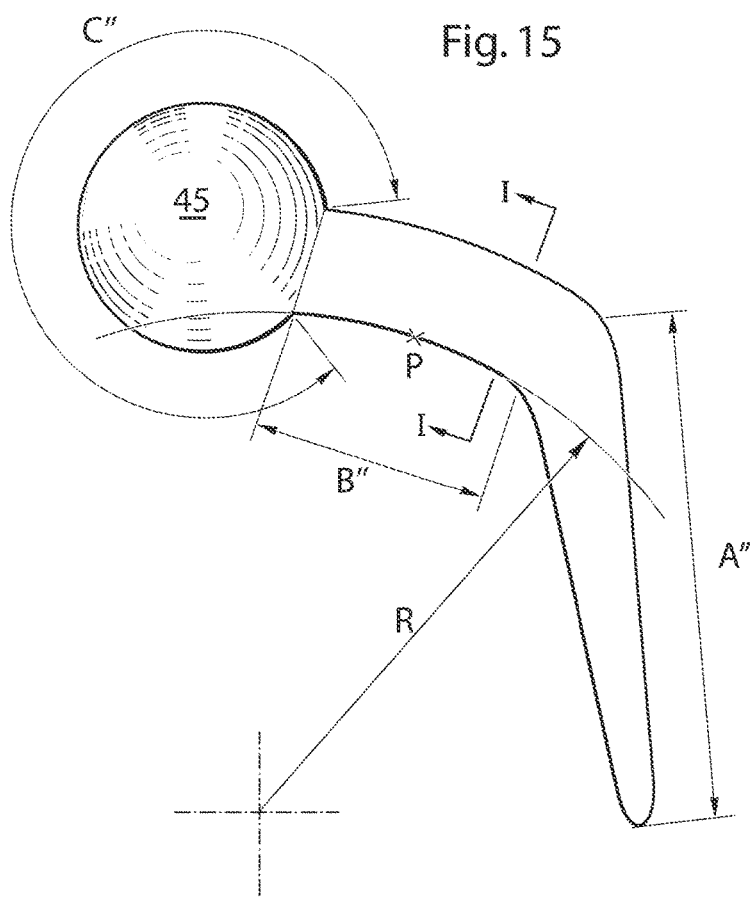
FIG. 15 shows the hip joint prosthesis having a curvature, FIG. 15' shows, schematically, how torsion affects a portion of a hip joint prosthesis.
Figure 15:
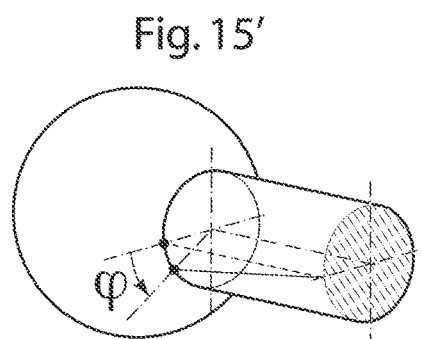

FIG. 15 shows the hip joint prosthesis according to an embodiment in which the hip joint prosthesis is adapted to absorb a force in the hip joint, through the hip joint prosthesis deforming elastically when exposed to a force. According to the embodiment shown in FIG. 15 the fixation section A" of the prosthesis comprises a material or part of material adapted to deform elastically when exposed to a force, and the intermediary section B" of the hip joint prosthesis comprises a material or part of material deforming more elastically than the material of the fixating section A".

The intermediary section B" of the hip joint prosthesis is adapted to absorb a force trough the intermediary section bending to a curvature having the curvature value $\kappa=1/R$, where R is the radius of the osculating circle in a point P on the curvature. According to one embodiment the hip joint prosthesis is adapted to be able to manage the intermediary section bending to a curvature value $\kappa>2$ whilst still having the fixating section A" fixedly attached to the femoral bone, and the femoral bone being intact. According to another embodiment the hip joint prosthesis is adapted to be able to manage the intermediary section bending to a curvature value $\kappa>4$ whilst still having the fixating section A" fixedly attached to the femoral bone, and the femoral bone being intact, and according to yet another embodiment the hip joint prosthesis is adapted to be able to manage the intermediary section bending to a curvature value $\kappa>8$ whilst still having the fixating section A" fixedly attached to the femoral bone, and the femoral bone being intact. All of the embodiments above is enabled through the intermediary section B" comprising a material elastic enough to absorb said force without injuring the femoral bone or the connection between the femoral bone and the hip joint prosthesis.

The hip joint prosthesis of FIG. 15 is further adapted to absorb a force in the hip joint through the intermediary section B" being able to twist elastically. The ability of a material to absorb torsion through twisting could be defined as the material ability to twist a certain angle i.e. angle of twist=$\varphi$, when a certain force is applied. According to one embodiment the hip joint prosthesis is adapted to be able to manage the intermediary section B" twisting to an angle of twist $\varphi>0.005\pi$ radians whilst still having the fixating section A" fixedly attached to the femoral bone, and the femoral bone being intact. According to another embodiment the hip joint prosthesis is adapted to be able to manage the intermediary section B" twisting to an angle of twist $\varphi>0.01\pi$ radians whilst still having the fixating section A" fixedly attached to the femoral bone, and the femoral bone being intact, and according to yet another embodiment the hip joint prosthesis is adapted to be able to manage the intermediary section B" twisting to an angle of twist $\varphi>0.02\pi$ radians whilst still having the fixating section A" fixedly attached to the femoral bone, and the femoral bone being intact. The angle of twist is displayed in FIG. 15'. All of the embodiments above is enabled through the intermediary section B" comprising a material elastic enough to absorb said force without injuring the femoral bone or the connection between the femoral bone and the hip joint prosthesis.

The hip joint prosthesis according to any of the embodiments could be adapted to bend elastically or twist elastically or bend and twist elastically. It is furthermore conceivable that the hip joint prosthesis according to any of the embodiments is adapted to twist elastically in the same way as the femoral bone and/or bend elastically in the same way as the femoral bone and/or the bone cement used to fixate the hip joint prosthesis to the femoral bone.

To improve the growth of bone tissue fixating the prosthesis, the fixating section, according to any of the embodiments could be made of a porous or partially porous material. The porous material allows the bone tissue to extend into the prosthesis and create a stabile fixation.

Please note that any embodiment or part of embodiment as well as any method or part of method could be combined in any way. All examples herein should be seen as a part of the general description and therefore possible to combine in any way in general terms.

The invention claimed is:

1. A hip joint prosthesis adapted to be implanted in a hip joint of a human patient, wherein said hip joint prosthesis has a length axis extending in a proximal-distal direction when implanted, wherein the hip joint prosthesis comprises a first proximal area and a second distal area, wherein said first proximal area comprises a first solid material having a first elasticity and said second distal area comprises a second solid material, having a second elasticity, wherein said first elasticity is different than said second elasticity, such that the difference in elasticity of the solid materials affects the elasticity of the hip joint prosthesis along the length axis thereof, and wherein the elasticity of a transition between the first proximal area and the second distal area varies continuously between the first elasticity and the second elasticity in a direction along said length axis, wherein said first solid material and said second solid material are a same solid material, wherein said first elasticity and said second elasticity is achieved by a hardening process.

2. The hip joint prosthesis according to claim 1, wherein said hip joint prosthesis further comprises a third, fourth and fifth area, and wherein:
said third area comprises a third solid material,
said fourth area comprises a fourth solid material,
said fifth area comprises a fifth solid material,
wherein said first, second, third, fourth and fifth solid materials are the same solid metal alloy, wherein said first, second, third, fourth and fifth solid materials have a different elasticity achieved by a hardening process, wherein said first, second, third, fourth and fifth solid materials are connected to each other through net attractive forces, and wherein said first, second, third, fourth, and fifth areas are placed consecutively along said length axis.

3. The hip joint prosthesis according to claim 2, wherein:
said first solid material is more elastic than said second solid material,
said second solid material is more elastic than said third solid material,
said third solid material is more elastic than said fourth solid material, and
said fourth solid material is more elastic than said fifth solid material.

4. The hip joint prosthesis according to claim 2, wherein:
said first solid material is more elastic than said second solid material, said second solid material is more elastic than said third solid material, said third solid material is less elastic than said fourth solid material, and said fourth solid material is less elastic than said fifth solid material.

5. The hip joint prosthesis according to claim 2, wherein:

said first solid material is more elastic than said second solid material, said second solid material is more elastic than said third solid material, said third solid material is more elastic than said fourth solid material, and said fourth solid material is less elastic than said fifth solid material.

6. The hip joint prosthesis according to claim 2, wherein:

said first area is the most proximal area of said first, second, third, fourth and fifth areas, said second area is the second most proximal area of said first, second, third, fourth and fifth areas, said third area is the third most proximal of said first, second, third, fourth and fifth areas, said fourth area is the fourth most proximal of said first, second, third, fourth and fifth areas, said fifth area is the fifth most proximal of said first, second, third, fourth and fifth areas, when said hip joint prosthesis is implanted is said human patient.

7. The hip joint prosthesis according to claim 6, wherein:

said first solid material is more elastic than said second solid material, said second solid material is more elastic than said third solid material, said third solid material is more elastic than said fourth solid material, and said fourth solid material is more elastic than said fifth solid material.

8. The hip joint prosthesis according to claim 6, wherein:

said first solid material is more elastic than said second solid material, said second solid material is more elastic than said third solid material, said third solid material is less elastic than said fourth solid material, and said fourth solid material is less elastic than said fifth solid material.

9. The hip joint prosthesis according to claim 6, wherein:

said first solid material is more elastic than said second solid material, said second solid material is more elastic than said third solid material, said third solid material is more elastic than said fourth solid material, and said fourth solid material is less elastic than said fifth solid material.

10. The hip joint prosthesis according to claim 1, wherein:

said hip joint of a human patient comprises an acetabulum, being a bowl shaped part of the pelvic bone, and wherein:

the proximal area comprises a connection section comprising a connection surface, said connection surface being formed of the first solid material being adapted to be in connection with said acetabulum, or an artificial replacement thereof, and the distal area comprises a fixating section comprising a fixating surface, said fixating surface being formed of the second solid material and being adapted to assist in the fixation of said hip joint prosthesis to the femoral bone of said human patient.

11. The hip joint prosthesis according to claim 10, wherein:

the first solid material and the second solid material are the same solid metal alloy, wherein said difference in elasticity of the solid materials is achieved by a hardening process, and wherein said elasticity of said first solid material is lower than said elasticity of said second solid material.

12. The hip joint prosthesis according to claim 10, wherein said first solid material and said second solid material are the same solid metal alloy, wherein the hip joint prosthesis further comprises an interconnecting part placed between said connection surface and said fixating surface, said interconnecting part comprising a third solid material which is the same solid metal alloy as said first solid material and said second solid material, wherein an elasticity of said third solid material is different than said elasticity of said first and second solid material, wherein said different elasticity between said third and said first and second solid material is achieved by a hardening process, wherein the elasticity of said third solid material is higher than the elasticity of said first and second solid materials.

13. The hip joint prosthesis according to claim 10, wherein said fixating section is adapted to be fixated to at least one of:

the collum femur, the collum femur, on the inside thereof, the femoral bone, and the femoral bone, on the inside thereof.

14. The hip joint prosthesis according to claim 10, wherein said connecting section comprises at least one of:

a ceramic material, and titanium carbide.

15. The hip joint prosthesis according to claim 1, wherein said hip joint prosthesis comprises at least one of:

steel, a biocompatible metal, steel in which the percentage of martensite is higher in a first solid surface material than in a second solid surface material, and a polymer material.

16. The hip joint prosthesis according to claim 1, wherein the distal area comprises a fixating section and the proximal area comprises a connecting section, and wherein the hip joint prosthesis further comprises an intermediary section placed between said fixating section and said connecting section, wherein said hip joint prosthesis is adapted to deform elastically when exposed to a force by said intermediary section being adapted to at least one of:

bend to a curvature when exposed to a force, twist when exposed to a force, and bend to a curvature and twist when exposed to a force.

17. The hip joint prosthesis according to claim 16, wherein said intermediary section is configured to bend to a curvature with one of:

κ>2, while said fixating section remains fixedly attached to the femoral bone,

κ>4, while said fixating section remains fixedly attached to the femoral bone, and κ>8, while said fixating section remains fixedly attached to the femoral bone.

18. The hip joint prosthesis according to claim 16, wherein said intermediary section is adapted to twist to an angle of twist selected from a group of angles of twist including:

$(\varphi)>0.005\pi$ while said fixating section remains fixedly attached to the femoral bone, $(\varphi)>0.01\pi$ while said fixating section remains fixedly attached to the femoral bone, and $(\varphi)>0.02\pi$ while said fixating section remains fixedly attached to the femoral bone.

19. The hip joint prosthesis according to claim 16, wherein said intermediary section is adapted to bend to a curvature with $\kappa>2$, and twist to an angle of twist $(\varphi)>0.005\pi$ while said fixating section remains fixedly attached to the femoral bone.

* * * * *